United States Patent [19]

Patel et al.

[11] Patent Number: 5,523,430

[45] Date of Patent: Jun. 4, 1996

[54] PROTEIN FARNESYL TRANSFERASE INHIBITORS

[75] Inventors: Dinesh V. Patel, Fremont, Calif.; Scott A. Biller, Ewing, N.J.; Eric M. Gordon, Palo Alto, Calif.

[73] Assignee: Bristol-Myers Squibb Company, New York, N.Y.

[21] Appl. No.: 247,743

[22] Filed: May 23, 1994

Related U.S. Application Data

[63] Continuation-in-part of Ser. No. 227,815, Apr. 14, 1994, abandoned.

[51] Int. Cl.⁶ .................................................. C07C 233/00
[52] U.S. Cl. .................. 554/40; 554/63; 554/78; 554/84
[58] Field of Search .................. 554/78, 40, 63, 554/84

[56] References Cited

U.S. PATENT DOCUMENTS

| 2,973,380 | 2/1961 | Swern et al. | 554/78 |
| 5,298,655 | 3/1994 | Anthony et al. | 562/598 |
| 5,326,773 | 7/1994 | deSolms et al. | 514/336 |

FOREIGN PATENT DOCUMENTS

| 91305283 | 12/1991 | European Pat. Off. |
| 91311658 | 7/1992 | European Pat. Off. |
| 92202924 | 9/1992 | European Pat. Off. |
| 92202923 | 9/1992 | European Pat. Off. |
| 92305926 | 12/1992 | European Pat. Off. |
| 92305925 | 1/1993 | European Pat. Off. |
| PCT/US91/02650 | 10/1991 | WIPO. |
| PCT/US93/05958 | 1/1994 | WIPO. |
| PCT/US93/06990 | 2/1994 | WIPO. |

OTHER PUBLICATIONS

Y. Reiss et al., Proc. Natl. Acad. Sci., vol. 88, 732–736, (1991).
S. L. Moores et al., The Journal of Biological Chemistry, vol. 266, 14603–14610, (1991).
J. B. Gibbs et al., The Journal of Biological Chemistry, vol. 268, 7617–7620, (1993).
Y. Reiss et al., Cell, vol. 62, 81–88, (1990).
D. L. Pompliano et al., Biochemistry, vol. 319, 3800–3807, (1992).
P. D. Milano et al., Abstract Paper, Am. Chem. Soc., vol. 203, 1–3, (1992).
J. L. Goldstein et al., The Journal of Biological Chemistry, vol. 266, 15575–15578, (1991).
J. F. Hancock et al., The EMBO Journal, vol. 10, 641–646, (1991).
Y. Reiss et al., The Journal of Bilogical Chemistry, vol. 266, 10672–10677, (1991).
L. D. Arnold et al., J. Am. Chem. Soc., vol. 109, 4649–4659, (1987).
L. D. Arnold et al., J. Am. Chem. Soc., vol. 107, 7105–7109, (1985).

*Primary Examiner*—José G. Dees
*Assistant Examiner*—Deborah D. Carr
*Attorney, Agent, or Firm*—Frank P. Hoffman

[57] ABSTRACT

Inhibition of farnesyl transferase, which is an enzyme involved in ras oncogene expression, and inhibition of cholesterol biosynthesis, are effected by compounds of the formula

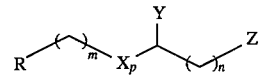

their enantiomers, diastereomers, and pharmaceutically acceptable salts, prodrugs, and solvates, wherein:

X is —ONR$^1$C(O)—, —N(OR$^1$)C(O)—, —NR$^1$C(O)—, —C(O)NR$^1$—, —NR$^1$S(O$_2$)—, —C(O)O—, —OC(O)—, —O—, —NR$^1$— or —(S)q;

Y and Z are each independently —CO$_2$R$^2$, —SO$_3$R$^2$ or —P(O)(OR$^2$)(OR$^3$);

R is alkyl, substituted alkyl, alkenyl, substituted alkenyl, alkenylene or aryl;

R$^1$, R$^2$ and R$^3$ are each independently hydrogen, alkyl, aryl or aralkyl;

m and n are each independently 0 or an integer from 1 to 5;

p is 0 or 1; and q is an integer from 1 to 2.

12 Claims, No Drawings

PROTEIN FARNESYL TRANSFERASE INHIBITORS

FIELD OF THE INVENTION

This application is a continuation-in-part of application Ser. No. 08/227,815 filed on Apr. 14, 1994 now abandoned. The entire contents of the parent application are hereby incorporated by reference.

This invention relates to compounds that inhibit farnesyl-protein transferase and Ras protein farnesylation, thereby making them useful as anti-cancer agents. The compounds are also useful in the treatment of diseases, other than cancer, associated with signal transduction pathways operating through Ras and those associated with CAAX-containing proteins other than Ras that are also post-translationally modified by the enzyme farnesyl protein transferase. The compounds may also act as inhibitors of other prenyl transferases, and thus be effective in the treatment of diseases associated with other prenyl modifications of proteins. These compounds additionally are useful in inhibiting cholesterol biosynthesis by inhibiting squalene synthetase (synthase), in hypocholesterolemic and antiatherosclerotic compositions and in a method for inhibiting cholesterol biosynthesis and atherosclerosis.

BACKGROUND OF THE INVENTION

The mammalian ras gene family comprises three genes, H-ras, K-ras and N-ras. The Ras proteins are a family of GTP-binding and hydrolyzing proteins that regulate cell growth and differentiation. Overproduction of normal Ras proteins or mutations that inhibit their GTPase activity can lead to uncontrolled cell division.

The transforming activity of Ras is dependent on localization of the protein to plasma membranes. This membrane binding occurs via a series of post-translational modifications of the cytosolic Ras proteins. The first and mandatory step in this sequence of events is the farnesylation of these proteins. The reaction is catalyzed by the enzyme farnesyl protein transferase (FPT), and farnesyl pyrophosphate (FPP) serves as the farnesyl group donor in this reaction. The Ras C-terminus contains a sequence motif termed a "Cys-Aaa$_1$-Aaa$_2$-Xaa" box (CAAX box), wherein Cys is cysteine, Aaa is an aliphatic amino acid, and Xaa is a serine or methionine. Farnesylation occurs on the cysteinyl residue of the CAAX box (Cys-186), thereby attaching the prenyl group on the protein via a thio-ether linkage.

Squalene synthetase is a microsomal enzyme which catalyzes the reductive dimerization of two molecules of farnesyl pyrophosphate (FPP) in the presence of nicotinamide adenine dinucleotide phosphate (reduced form)(NADPH) to form squalene (Poulter, C. D.; Rilling, H. C., in "Biosynthesis of Isoprenoid Compounds", Vol. I, Chapter 8, pp. 413–441, J. Wiley and Sons, 1981, and references therein). This enzyme is the first committed step of the de novo cholesterol biosynthetic pathway. The selective inhibition of this step should allow the essential pathways to isopentenyl tRNA, ubiquinone, and dolichol to proceed unimpeded. Squalene synthetase along with HMG-CoA reductase have been shown to be down-regulated by receptor mediated LDL uptake (Faust, J. R.; Goldstein, J. L.; Brown, M. S. *Proc. Nat. Acad. Sci. U.S.A.* 1979, 76, 5018–5022), lending credence to the proposal that inhibiting squalene synthetase will lead to an up-regulation of LDL receptor levels, as has been demonstrated for HMG-CoA reductase, and thus ultimately should be useful for the treatment and prevention of hypercholesterolemia and atherosclerosis.

BRIEF DESCRIPTION OF THE INVENTION

In accordance with the present invention, a compound of the formula

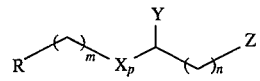

its enantiomers and diastereomers, and pharmaceutically acceptable salts, prodrugs and solvates thereof inhibit S-farnesyl protein transferase, which is an enzyme involved in Ras oncogene function, and inhibit cholesterol biosynthesis. In formula I and throughout this specification, unless otherwise specified, the above symbols are defined as follows:

X is —ONR$^1$C(O)—, —N(OR$^1$)C(O)—, —NR$^1$C(O)—, —C(O)NR$^1$—, —NR$^1$S(O$_2$)—, —C(O)O—, —OC(O)—, —O—, —NR$^1$— or —(S)q;

Y and Z are each independently —CO$_2$R$^2$, —SO$_3$R$^2$ or —P(O)(OR$^2$)(OR$^3$);

R is alkyl, substituted alkyl, alkenyl, substituted alkenyl, alkenylene or aryl;

R$^1$, R$^2$ and R$^3$ are each independently hydrogen, alkyl, aryl or aralkyl;

m and n are each independently 0 or an integer from 1 to 5;

p is 0 or 1; and q is an integer from 1 to 2.

DETAILED DESCRIPTION OF THE INVENTION

Definition of Terms

Listed below are definitions of various terms used to describe this invention. These definitions apply to the terms as they are used throughout this specification, unless otherwise limited in specific instances, either individually or as part of a larger group.

The expression "alkyl" refers to straight or branched chain unsubstituted hydrocarbon groups of 1 to 20 carbon atoms, preferably 1 to 15 carbon atoms. The expression "lower alkyl" refers to unsubstituted alkyl groups of 1 to 4 carbon atoms.

The expression "substituted alkyl" refers to an alkyl group substituted by, for example, one to four substituents such as halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, N-hydroxycarbamyl, alkoxycarbonyl, phenyl, substituted phenyl, guanidino, indolyl, imidazolyl, furyl, thienyl, thiazolyl, pyrrolidyl, pyridyl, pyrimidyl and the like.

The term "alkylene" refers to a straight chain bridge of 1 to 20 carbon atoms, preferably 1 to 12 carbon atoms, connected by single bonds, which may be substituted by 1 to 5 lower alkyl groups, preferably 1 to 3 lower alkyl groups.

The term "alkenyl" refers to straight or branched chain unsubstituted hydrocarbon groups of 2 to 20 carbon atoms, preferably 2 to 15 carbon atoms, having at least one double bond.

The expression "substituted alkenyl" refers to an alkenyl group substituted by, for example, one to four substituents identified for substituted alkyl.

The term "alkenylene" refers to a straight chain bridge of 1 to 20 carbon atoms, preferably 1 to 13 carbon atoms, having 1 to 5 double bonds, preferably 1 to 3 double bonds, which may be substituted by 1 to 5 lower alkyl groups, preferably 1 to 3 lower alkyl groups. Exemplary alkenylene groups are: farnesyl and geranyl.

The term "halogen" or "halo" refers to fluorine, chlorine, bromine and iodine.

The term "alkoxy" refers to alkyl-O—.

The term "alkanoyl" refers to alkyl-C(O)—.

The term "alkanoyloxy" refers to alkyl-C(O)—O—.

The terms "alkylamino" and "dialkylamino" refer to (alkyl)NH— and (alkyl)$_2$N—, respectively.

The term "alkanoylamino" refers to alkyl-C(O)—NH—.

The term "alkylthio" refers to alkyl-S—.

The term "alkylthiono" refers to alkyl-S(O)—.

The term "alkylsulfonyl" refers to alkyl-S(O)$_2$—.

The term "carbamyl" refers to —C(O)NH$_2$.

The term "alkoxycarbonyl" refers to alkyl-O—C(O)—.

The term "aryl" refers to phenyl, napthyl, biphenyl and diphenyl groups, each of which may be substituted;

The term "aralkyl" refers to an aryl group bonded directly through an alkyl group, e.g., benzyl.

The expression "substituted phenyl" refers to a phenyl group substituted by, for example, one to four substituents such as alkyl, halo, hydroxy, alkoxy, alkanoyl, alkanoyloxy, amino, alkylamino, dialkylamino, alkanoylamino, thiol, alkylthio, nitro, cyano, carboxy, carbamyl, alkoxycarbonyl, alkylthiono, alkylsulfonyl, sulfonamido and the like.

The compounds of formula I form salts which are also within the scope of this invention. Pharmaceutically acceptable (i.e., non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts may be obtained by exchanging, for example, the carboxylic acid protons in compound I with the desired ion in a medium in which the salt precipitates or in an aqueous medium followed by evaporation.

When compound I comprises a basic moiety, such as amino or substituted amino, it may form salts with a variety of organic and inorganic acids. Such salts include those formed with hydrogen chloride, hydrogen bromide, methanesulfonic acid, sulfuric acid, acetic acid, trifluoroacetic acid, maleic acid, benzenesulfonic acid, toluenesulfonic acid and various others (e.g., nitrates, phosphates, borates, tartrates, citrates, succinates, benzoates, ascorbates, salicylates and the like). Such salts may be formed by reacting compound I in an equivalent amount of the acid in a medium in which the salt precipitates or in an aqueous medium followed by evaporation.

In addition, zwitterions ("inner salts") may be formed.

It should be understood that the present invention is meant to include prodrug forms of the compounds of the formula I. While prodrug forms of the compounds of formula I are generally already represented herein (e.g., where Y and Z are —CO$_2$R$^2$ and R$^2$ is alkyl), it is understood that any moiety at the Y or Z position that will be cleaved in vivo to provide an acidic moiety is within the scope and spirit of the invention. For example, compound I may be in the form of a prodrug having the formula

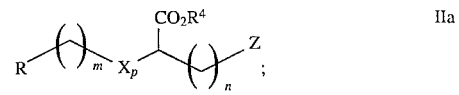 IIa

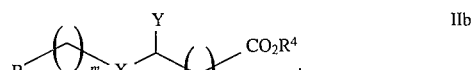 IIb

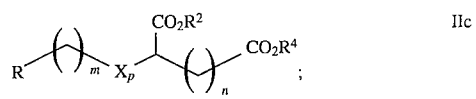 IIc

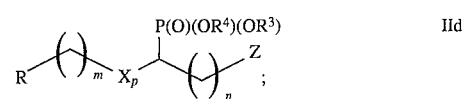 IId

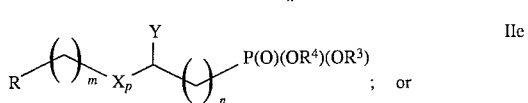 IIe

; or

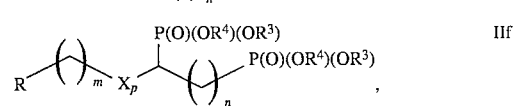 IIf wherein R$^4$ is:

lower alkyl, such as methyl, ethyl and the like;

substituted lower alkyl, such as 2-(N-morpholine)ethyl and the like;

lower aralkyl, such as benzyl, biphenylmethyl and the like;

(acyloxy)alkyl, such as (pivalyloxy)methyl, 1-(propanoyloxy)-2-methyl-1-propyl and the like;

(aminoacyloxy)aroyloxyalkyl, such as para-glycyloxybenzoyloxymethyl and the like;

(aminoalkoxy)aroyloxyalkyl, such as para-2-[(N-morpholine)ethoxy]benzoyloxymethyl and the like;

substituted amides, such as N,N-di(2-hydroxyethyl)acetamido, 4-methylpiperazine-1-acetyl, 4-(2-hydroxyethyl)piperazine-1-acetyl and the like; or a dioxolanemethyl, such as (5-methyl-2-oxo-1,3-dioxolan-4-yl)methyl and the like.

Various forms of prodrugs are well known in the art. For examples of such prodrug derivatives, see:

a) *Design of Prodrugs*, edited by H. Bundgaard, (Elsevier, 1985) and *Methods in Enzymology*, Vol. 42, p. 309–396, edited by K. Widder, et al. (Academic Press, 1985);

b) *A Textbook of Drug Design and Development*, edited by Krogsgaard-Larsen and H. Bundgaard, Chapter 5, "Design and Application of Prodrugs," by H. Bundgaard, p. 113–191 (1991);

c) H. Bundgaard, *Advanced Drug Delivery Reviews*, 8, 1–38 (1992);

d) H. Bundgaard, et al., *Journal of Pharmaceutical Sciences*, 77, 285 (1988); and e) N. Kakeya, et al., *Chem Pharm Bull*, 32, 692 (1984).

It should further be understood that solvates (e.g., hydrates) of the compounds of formula I are also within the scope of the present invention. Methods of solvation are generally known in the art. Similarly, enantiomers and diastereomers of the compounds of formula I are within the scope of the present invention.

Preferred Moieties

For compounds of the formula I, the following moieties are preferred:

X is —$ONR^1C(O)$—, —$NR^1C(O)$—, —$C(O)NR^1$—, —O— or —$NR^1$— when p is 1;

Y is —$CO_2R^2$;

Z is —$CO_2R^2$ or —$P(O)(OR^2)(OR^3)$;

R is alkenylene, cinnamoyl or prenyl;

$R^1$ is hydrogen or lower alkyl;

$R^2$ and $R^3$ are each hydrogen; and n is 1 or 2.

The following moieties are particularly preferred:

X is —$ONHC(O)$—, —$NHC(O)$—, —$NCH_3C(O)$—, —$C(O)NH$—, —O— or —NH— when p is 1;

Y is —$CO_2H$;

Z is —$CO_2H$ or —$P(O)(OH)(OH)$;

R is alkenylene; and n is 1 or 2.

In particular, R is alkenylene of 8 to 15 carbon atoms.

Use and Utility

The compounds of formula I are inhibitors of S-farnesyl protein transferase. They are thus useful in the treatment of a variety of cancers, including (but not limited to) the following:

carcinoma, including that of the bladder, breast, colon, kidney, liver, lung, ovary, pancreas, stomach, cervix, thyroid and skin;

hematopoietic tumors of lymphoid lineage, including acute lymphocytic leukemia, B-cell lymphoma and Burketts lymphoma;

hematopoietic tumors of myeloid lineage, including acute and chronic myelogenous leukemias and promyelocytic leukemia;

tumors of mesenchymal origin, including fibrosarcoma and rhabdomyosarcoma; and other tumors, including melanoma, seminoma, tetratocarcinoma, neuroblastoma and glioma.

The compounds of formula I are especially useful in treatment of tumors having a high incidence of Ras involvement, such as colon, lung, and pancreatic tumors. By the administration of a composition having one (or a combination) of the compounds of this invention, development of tumors in a mammalian host is reduced.

Compounds of formula I may also be useful in the treatment of diseases other than cancer that may be associated with signal transduction pathways operating through Ras, e.g., neuro-fibromatosis.

Compounds of formula I may also be useful in the treatment of diseases associated with CAAX-containing proteins other than Ras (e.g., nuclear lamins and transducin) that are also post-translationally modified by the enzyme farnesyl protein transferase.

Compounds of formula I may also act as inhibitors of other prenyl transferases (e.g., geranylgeranyl transferase), and thus be effective in the treatment of diseases associated with other prenyl modifications (e.g., geranylgeranylation) of proteins (e.g., the rap, rab, rac and rho gene products and the like). For example, they may find use as drugs against Hepatitis delta virus (HDV) infections, as suggested by the recent finding that geranylgeranylation of the large isoform of the delta antigen of HDV is a requirement for productive viral infection [J. S. Glenn, et al., *Science*, 256, 1331 (1992)].

The compounds of this invention may also be useful in combination with known anti-cancer and cytotoxic agents. If formulated as a fixed dose, such combination products employ the compounds of this invention within the dosage range described below and the other pharmaceutically active agent within its approved dosage range. Compounds of formula I may be used sequentially with known anticancer or cytotoxic agents when a combination formulation is inappropriate.

The compounds of formula I of the invention additionally inhibit cholesterol biosynthesis by inhibition of de novo squalene production. These compounds inhibit the squalene synthetase enzyme and, in addition, some of the compounds of formula I of the invention inhibit other enzymes in the pathway from isopentenyl diphosphate to squalene, that is, farnesyl diphosphate synthetase and isopentenyl diphosphatedimethylallyl diphosphate isomerase.

Thus, the compounds of the invention are useful in treating atherosclerosis to inhibit progression of disease and in treating hyperlipidemia to inhibit development of atherosclerosis. In addition, the compounds of the invention may increase plasma high density lipoprotein cholesterol levels.

The compounds of the invention may also be employed in combination with an antihyperlipoproteinemic agent such as probucol and/or with one or more serum cholesterol lowering agents such as Lopid (gemfibrozil), bile acid sequestrants such as cholestyramine, colestipol, polidexide (DEAE-Sephadex) as well as clofibrate, nicotinic acid and its derivatives, neomycin, p-aminosalicyclic acid, bezafibrate and the like and/or one or more HMG CoA reductase inhibitors such as lovastatin, pravastatin, velostatin or simvastatin.

The compounds of this invention may be formulated with a pharmaceutical vehicle or diluent for oral, intravenous or subcutaneous administration. The pharmaceutical composition can be formulated in a classical manner using solid or liquid vehicles, diluents and additives appropriate to the desired mode of administration. Orally, the compounds can be administered in the form of tablets, capsules, granules, powders and the like. These compounds may be administered in a dosage range of about 0.05 to 50 mg/kg/day, preferably less than 50 mg/kg/day, in a single dose or in 2 to 4 divided doses. The compounds of the invention may also be employed with sodium lauryl sulfate or other pharmaceutically acceptable detergents to enhance oral bioavailability of such compounds.

Inhibition of squalene synthetase may be measured by the following procedure.

Rat liver microsomal squalene synthetase activity is measured using farnesyl diphosphate as substrate and quantitating squalene synthesis using gas chromatographic analysis. The assay was developed by modifying conditions originally described by Agnew (Methods in Enzymology 110:357, 1985). Alternatively, squalene synthetase activity can be measured by the procedure of C. P. Ciosek et al., *J. Biol. Chem.*, 268, 24832–24837, 1993.

Process of Preparation

The compounds of the invention can be prepared according to the following general reaction schemes:

Scheme I

Coupling a carboxylic acid of the formula III:

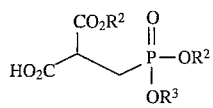

with an amine of the formula IV:

provides the amide of formula V:

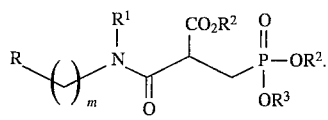

A variety of coupling reagents may be used for this coupling, including 1-(3-dimethylaminopropyl)-3-ethylcarbodiimide hydrochloride (EDC) with 1-hydroxybenzotriazole (HOBt), dicyclohexylcarbodiimide (DCC) with HOBt, benzotriazol-1-yloxytris(dimethylamino)phosphonium hexafluorophosphate (BOP) with or without HOBt, carbonyldiimidazole (CDI), DCC and pentafluorophenol, bis(2-oxo-3-oxazolidinyl)phosphinic chloride (BOP chloride), isopropylchloroformate (IPCF) and the like. An acid chloride derivative of a compound of the formula III may also be used directly in the presence of an alkali metal (e.g., potassium carbonate) or an organic base (e.g., diisopropylethylamine) in an organic solvent (e.g., dimethylformamide (DMF), tetrahydrofuran (THF), dichloromethane and the like) in this coupling reaction to provide a compound of the formula V.

Deprotection of a compound of the formula V provides a compound of the formula I where X is

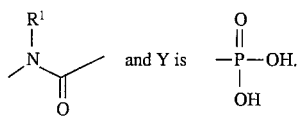

Similarly, the use of a compound of the formula IVa:

in place of an amine of the formula IV provides a compound of the formula I where X is

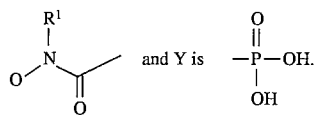

Scheme II

An amine of the formula VI can be prepared as described in the art (for example, see J. M. Varlet, et al., *Can J. Chem.*, 1979, 57, 3216):

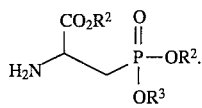

Coupling of an amine of the formula VI with a carboxylic acid of the formula VII:

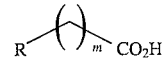

provides an amide of the formula VIII:

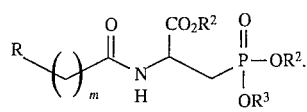

Deprotection of a compound of the formula VIII provides a compound of the formula I where X

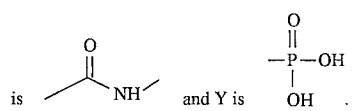

Scheme III

An amine of the formula IX is either commercially available or can be prepared by methods known in the art:

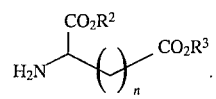

Coupling of an amine of the formula IX with a carboxylic acid of the formula VII provides the amide of formula X:

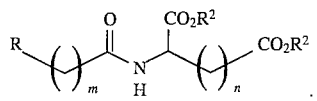

Deprotection of a compound of the formula X provides a compound of the formula I where X is

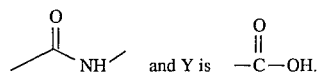

Scheme IV

The ester of the formula III can be reacted with an alkylating agent of the formula XI wherein L is a suitable leaving group (e.g., halide, tosylate, mesylate, triflate and the like):

in the presence of a suitable base (e.g., sodium hydride) to provide a compound of the formula XII:

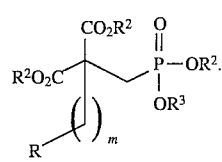

Selective hydrolysis of a compound of the formula XII, followed by decarboxylation by methods known in the art, provides a compound of the formula XIII:

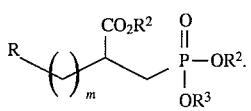

Deprotection of a compound of the formula XIII provides a compound of the formula I where X is

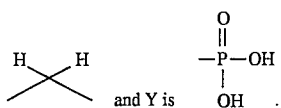 and Y is $-\overset{O}{\underset{OH}{\overset{\|}{P}}}-OH$ .

A compound of the formula XIII may also be prepared in the following manner:

The triester of the formula XIV:

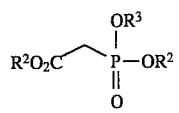  XIV may be alkylated with a compound of the formula XI to provide a compound of the formula VX:

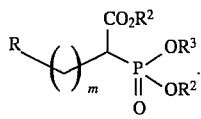  XV

Condensation of a compound of the formula XV with formaldehyde, followed by heating as described in the art (J. Villieras, et al., *Synthesis*, 1984, 406) provides the unsaturated ester of the formula XVI:

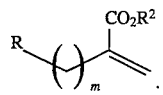  XVI

Michael addition of a dialkylphosphite of the formula XVII:

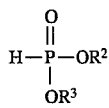  XVII to a compound of the formula XVI provides a compound of the formula XIII.

Scheme V

Diazoetherification of an alcohol of the formula XVIII:

  XVIII with a dialkyldiazomalonate of the formula XIX:

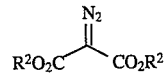  XIX provides an ether of the formula XX:

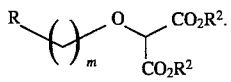  XX

A Mannich type reaction of a compound of the formula XX with N,N-dimethylmethyleneammonium iodide provides the intermediate XXI:

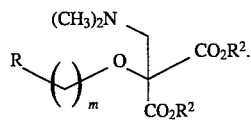  XXI

Reaction of a compound of the formula XXI with methyliodide, followed by treatment of the resulting methiodide salt with mild base (1 equivalent), provides a compound of the formula XXII:

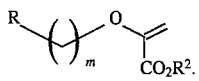  XXII

Michael addition of a dialkylphosphite of the formula XVII to the unsaturated ester of the formula XXII provides a compound of the formula XXIII:

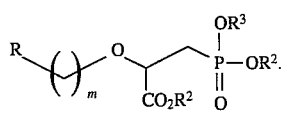  XXIII

Deprotection of a compound of the formula XXIII provides a compound of the formula I where X is —O— and Y is

Scheme VI

Alkylation of an amine of the formula VI with a compound of the formula XI by employing methods known in the art gives a compound of the formula XXIV:

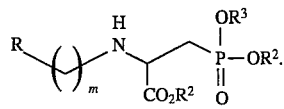  XXIV

Deprotection of a compound of the formula XXIV provides a compound of the formula I where X is

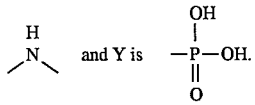

Scheme VII

A compound of the formula XI can be reacted with a compound of the formula XXV:

  XXV in the presence of a suitable base (e.g., sodium hydride) to provide a compound of the formula XXVI:

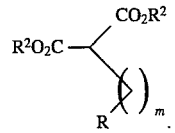  XXVI

A compound of the formula XXVI can be reacted with a compound of the formula XXVII:

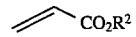  XXVII in the presence of a suitable base (e.g., potassium t-butoxide) to provide a compound of the formula XXVIII:

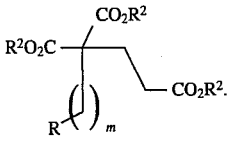  XXVIII

Selective hydrolysis of a compound of the formula XXVIII, followed by decarboxylation by methods known in the art, provides a compound of the formula XXIX:

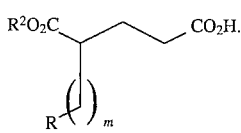

Hydrolysis of a compound of the formula XXIX provides a compound of the formula I where X is

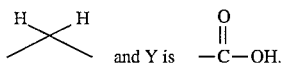

In compounds of the formulas V, VIII, X, XIII, XXIII and XXIV, the carboxylic and/or phosphonic acid protecting groups may be removed by methods known in the art to provide the compound of the general formula I as noted above. The phosphonate diesters can be converted to the corresponding phosphonic diacids by treatment with bromotrimethylsilane (TMSBr) in dichloromethane in the presence of an acid scavenger like bis(trimethylsilyl)trifluoroacetamide (BSTFA). The carboxylic esters can converted to the acids by basic hydrolysis (e.g., with sodium hydroxide/methanol).

Protecting groups may be used in these processes with substituents having reactive functionalities, such as hydroxyl, carboxyl, amino, mercapto, guanidino, imidazolyl, indolyl and the like. The particular protecting groups used depend upon the reactive functionality to be protected and are generally known in the art. Exemplary sidechain protecting groups include acetyl, benzoyl, benzyl, t-butyl and the like for hydroxyl; cyclohexyl, benzyl, methyl, ethyl, t-butyl and the like for carboxyl; benzyl, 4-methylbenzyl, 4-methoxybenzyl, acetyl, acetamidomethyl, triphenylmethyl (trityl) and the like for mercapto; t-butoxycarbonyl (Boc), benzyloxylcarbonyl (Cbz), N-[(9H-Fluoren-9-ylmethoxy)carbonyl](Fmoc), phthaloyl (Pht), p-toluenesulfonyl (Tos), trifluoroacetyl, 2-(trimethylsilyl)ethoxycarbonyl (Teoc) and the like for amino; 2,4-dinitrophenyl, benzyloxymethyl, Tos, Boc, trityl and the like for imidazolyl; formyl, Cbz, Teoc, 2,2,2-trichloroethyl carbamate (TROC) and the like for indolyl; and tosyl, nitro, bis(1-adamantyloxycarbonyl) and the like for guanidino.

Side-chain protecting groups may be removed, if desired, by, for example, treatment with one or more deprotecting agents in an inert solvent or solvent mixture. For examples of protecting groups and suitable deprotecting agents, see M. Bodansky and A. Bodansky, "The Practice of Peptide Synthesis", Springer-Verlag, Inc. (1984); and T. W. Greene and P. G. M. Wuts, "Protective Groups in Organic Synthesis", Second Edition, John Wiley & Sons, New York, 1991.

The invention will now be further described by the following working examples, which are preferred embodiments of the invention. All temperatures are in degrees Celsius (°C.) unless otherwise indicated. Compounds exemplified herein, which comprise a basic moiety such as an amine or substituted amine, may exist as a salt of an organic or inorganic acid. This information is not necessarily explicitly described in all the examples, but would be understood by those skilled in the art. These examples are illustrative rather than limiting.

EXAMPLE 1

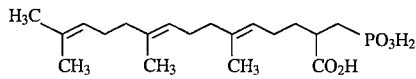

(E,E)-6,10,14-Trimethyl-2-(phosphonomethyl)-5,9,13-pentadecatrienoic acid, tripotassium salt A. (E,E)-6,10,14-Trimethyl-2-(diethylphosphono)-5,9,13-pentadecatrienoic acid, ethyl ester To 1.00 g (25.1 mmol) of 60% sodium hydride in mineral oil, pre-washed with pentane and suspended in 15 mL of tetrahydrofuran under argon was added dropwise 5.0 mL (25.1 mmol) of triethylphosphonoacetate. The resulting clear solution was stirred for ½ hour then treated with a solution of 2.91 g (8.37 mmol) of homofarnesyl iodide in 5 mL of tetrahydrofuran. The reaction was stirred for five hours at reflux. After cooling, the solution was quenched with hydrochloric acid and diluted with 50 mL of dichloromethane and 150 mL of ethyl ether, washed with water and brine, dried over magnesium sulfate and evaporated to obtain 6.08 g of an orange oil. Flash chromatography on 300 g of silica, eluted with 4:6 ethyl acetate:petroleum ether, provided 2.33 g (63%) of Compound A as a yellow oil.

TLC Silica gel (1:1 ethyl acetate:hexane) Rf=0.21.

B. (E,E)-6,10,14-Trimethyl-2-(methylenyl)-5,9,13-pentadecatrienoic acid, ethyl ester A mixture of 1.63 g (3.69 mmol) of Compound A, 1.53 g (11.1 mmol) of finely powdered potassium carbonate, and 6.7 mL of 37% aqueous formaldehyde was stirred at reflux under argon for 4.5 hours. After cooling and the addition of 3 mL of water, the mixture was extracted with three 40 mL portions of dichloromethane. The combined organic layers were washed with 40 mL of brine, dried over magnesium sulfate and evaporated to give 1.84 g of a colorless oil. Flash chromatography on 70 g of silica, eluted with 4:96 ethyl acetate:petroleum ether, provided 936 mg of Compound B as a colorless oil.

TLC Silica gel (5:95 ethyl aceate:hexane) Rf=0.31.

C. (E,E)-6,10,14-Trimethyl-2-(phosphonomethyl)-5,9,13-pentadecatrienoic acid, triethyl ester To a solution of 931 mg (2.92 mmol) of Compound B and 565 μL (4.38 mmol) of diethylphosphite in 10 mL of tetrahydrofuran under argon was added 35 mg (0.88 mmol) of a 60% suspension of sodium hydride in mineral oil. The reaction was stirred for two hours, then quenched with 5 mL of saturated ammonium chloride and 5 mL of water. The mixture was diluted with 40 mL of ethyl acetate, and the organic phase was washed with two 10 mL portions of water and 10 mL of brine, dried over magnesium sulfate and evaporated to yield 1.36 g of a colorless oil. Flash chromatography on 70 g of silica, eluted with 1:1 ethyl acetate:petroleum ether, provided 1.16 g (87%) of Compound C as a colorless oil.

TLC Silica gel (7:3 ethyl acetate:hexane) Rf=0.24.

D. (E,E)-6,10,14-Trimethyl-2-(phosphonomethyl)-5,9,13-pentadecatrienoic acid, tripotassium salt A solution of 580 mg (1.27 mmol) of Compound C and 255 μL (1.91 mmol) of collidine in 3 mL of dichloromethane was treated with 505 μL (3.81 mmol) of bromotrimethylsilane and stirred for five hours at room temperature under nitrogen. The mixture was evaporated and pumped at high vacuum. The residue was treated with 5.72 mL of 1M sodium hydroxide. The free phosphonic acid was formed by diluting with 20 mL of ethyl acetate and acidifying with aqueous hydrochloric acid. The aqueous phase was re-extracted with 20 mL of ethyl acetate and the combined organic phases were washed with brine, dried over magnesium sulfate and evaporated to provide the intermediate phosphonic acid-carboxylic ester. The intermediate was treated with 5.72 mL of 1M KOH and stirred for one hour at room temperature and six hours at 50° C. Additional 1.3 mL of 1M KOH was added and the reaction was stirred for 24 hours at 70° C. After cooling, the mixture was acidified with 10% hydrochloric acid and extracted with four 15 mL portions of ethyl acetate. The combined organic phase was washed with 5 mL of brine, dried over magnesium sulfate and evaporated. The tripotassium salt was formed by treating the free acid with slightly more than 3 eq. of 1M KOH and purified by HP-20 chromatography on a 2.5×20 cm column packed in water. The column was eluted with a gradient created by the gradual addition of 500 mL of acetonitrile to 500 mL of water. Fractions containing product were combined, evaporated, lyophilized and pump-dried 24 hours to provide 448 mg (73%) of the title compound as a very hygroscopic white lyophilate.

TLC Silica gel (6:3:1 n-propanol:concentrated ammonia:water) Rf=0.40.

Analysis Calculated for $C_{19}H_{30}O_5P.K_3$ (MW=486.724): Calculated: C, 46.89; H, 6.21; P, 6.36. Found: C, 47.46; H, 7.83; P, 6.43.

EXAMPLE 2

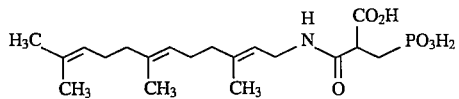

(E,E)-2-[(Dihydroxyphosphinyl)methyl]-3-oxo-3-[(3,7,11-trimethyl-2,6,10-dodecatrienyl)amino]-propanoic acid, trisodium salt A. (E,E)-2-[(Dihydroxyphosphinyl)methyl]-3-oxo-3-[(3,7,11-trimethyl-2,6,10-dodecatrienyl)amino]-propanoic acid, triethyl ester To a solution of 0.31 g (1.10 mmol) of O,O-diethylphosphonomethyl malonate, monoethyl ester in 3 mL of dichloromethane at 0° C. was added 2 drops of DMF, followed by the dropwise addition of 190 µl (2.2 mmol) of oxalyl chloride. The solution was warmed to 25° C., stirred for 2 hours and concentrated. To a solution of 312 mg (1.21 mmol) of 1-[(3,7,11-trimethyl)(2,6,10-dodecatrienyl)]amine in 3 mL of dichloromethane at 0° C. was added 570 µl (2.7 mmol) of diisopropylethylamine, cooled to 0° C., and the acid chloride formed from above in 3 mL of dichloromethane at 0° C. was added dropwise via cannula. The resulting solution was stirred for 45 minutes, then 30 mL of ethyl ether was added. The organic layer was washed successively with 15 mL each of 1N aqueous hydrochloric acid, water, saturated aqueous sodium bicarbonate and brine. The organic layer was dried (magnesium sulfate) and concentrated to yield a crude yellow-white oil. Flash chromatography on 60 mL of silica gel eluted with 2:1 ethyl acetate/petroleum ether, followed by filtration through Act III neutral alumina eluted with 3:1 ethyl acetate/petroleum ether afforded 0.34 g (65%) of Compound A as a yellow oil.

TLC: silica gel (3:1 ethyl acetate/petroleum ether) Rf=0.18.

B. (E,E)-2-[(Dihydroxyphosphinyl)methyl]-3-oxo- 3-[(3,7,11-trimethyl-2,6,10-dodecatrienyl)amino]-propanic acid, trisodium salt To a solution of 0.36 g (0.70 mmol) of Compound A in 2 mL of distilled dichloromethane was added dropwise 185 µL (1.4 mmol, distilled) of collidine, followed by 370 µL (2.8 mmol) of bromotrimethyl silane. The mixture was stirred at 25° C. for 2.25 hours, and concentrated. Benzene was added to the residue, the solution was concentrated, and the remainder was pumped at high vacuum. The residue was dissolved in 5.6 mL of 1N aqueous sodium hydroxide solution and stirred for 16 hours. The solution was lyophilized and the lyophilate was purified by chromatography on a 2.5×20 cm column of HP-20 packed in water. The column was eluted first with water to an eluant pH of 9–10 followed by 10% aqueous acetonitrile. The appropriate fractions were combined, evaporated, lyophilized and pump dried to provide 0.31 g (80%) of the title compound as a very hygroscopic white lyophilate.

TLC: silica gel (6:3:1 n-propanol:concentrated ammonia:water). Rf=0.35, $I_2$ and PMA. Analysis Calculated for $C_{19}H_{29}NO_6P.Na_3$ (MW=467.379): Calculated: C, 41.01; H, 7.04; N, 2.52. Found: C, 40.75; H, 6.89; N, 2.75.

EXAMPLE 3

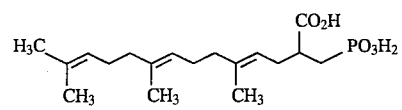

(E,E)-2-[(Dihydroxyphosphinyl)methyl]-5,9,13-trimethyl-4,8,12-tetradecatrienoic acid, trisodium salt A. (E,E)-2-[(Dihydroxyphosphinyl)methyl]-2 -(ethoxycarbonyl)-5,9,13-trimethyl-4,8,12 -tetradecatrienoic acid, triethyl ester To 45.5 mg (1.14 mmol) of a 60% sodium hydride suspension in mineral oil in 4 mL of tetrahydrofuran under argon was added 352 mg (1.14 mmol) of phosphonomethyl malonate, triethyl ester. The resultant solution was stirred 0.5 hours, then cooled to 0° C. A solution of 222 mg (0.76 mmol) of farnesyl bromide in 1 mL of tetrahydrofuran was slowly added. A white precipitate began forming within minutes. The mixture was stirred 0.5 hours at 0° C., then 2 hours at room temperature. The reaction was quenched with ammonium chloride, diluted with 20 ml of ethyl ether, washed with 5 ml of water and 5 ml of brine, dried over magnesium sulfate and evaporated to obtain 434 mg of crude compound. Chromatography on 30 g of silica, eluting with 4:6 ethyl acetate:petroleum ether, provided 202 mg (52%) of Compound A as a colorless oil.

TLC Silica gel (1:1 ethyl acetate:hexanes) Rf=0.19.

B. (E,E)-2-[(Dihydroxyphosphinyl)methyl]-5,9,13-trimethyl-4,8,12-tetradecatrienoic acid, triethyl ester A solution of 182 mg (0.35 mmol) of Compound A in a mixture of 0.70 mL of ethanol and 350 µL (0.70 mmol) of 2M sodium hydroxide was stirred for 24 hours. The reaction was acidified with 1M hydrochloric acid, and the ethanol was removed. The aqueous mixture was extracted with ethyl ether and the organic phase was washed with water and brine, dried over magnesium sulfate and evaporated to give 144 mg of the monocarboxylic acid. The residue was dissolved in 3 mL of xylenes and stirred for two hours at 100° C., for five hours at reflux, and for two days at room temperature. The solution was treated with 27 µL (0.18 mmol) of 1,8 -diazabicyclo[5.4.0]undec-7-ene and 56 µL (0.70 mmol) of iodoethane, and the mixture was heated to 70° C. for four hours. Additional 27 µL (0.18 mmol) of 1,8-diazabicyclo-[5.4.0]undec-7-ene and 28 µL (0.35 mmol) of iodoethane were added and the mixture was stirred one hour at 65° C. and 16 hours at room temperature. After cooling, the DBU.HI complex was filtered off and the solvent was evaporated to leave 133 mg of a yellow oil. Chromatography on 13 g of silica, eluted with 1:1 ethyl acetate:petroleum ether provided 88.1 mg (57%) of virtually pure monocarboxylate.

TLC Silica gel (1:1 ethyl acetate:hexane) Rf=0.10.

C. (E,E)-2-[(Dihydroxyphosphinyl)methyl]-5,9,13-trimethyl-4,8,12-tetradecatrienoic acid, trisodium salt A solution of 80.9 mg (0.18 mmol) of Compound B and 36 μL (0.27 mmol) of collidine in 500 μL of dichloromethane under nitrogen was treated with 72 μL (0.54 mmol) of bromotrimethylsilane. After 24 hours, additional 12 μL (0.09 mmol) of collidine and 24 μL (0.18 mmol) of bromotrimethylsilane were added. The reaction mixture was stirred for 3.5 hours, the solvent was evaporated, and the residue was pumped on for 0.5 hours. The residue was dissolved in 1.45 mL (1.45 mmol) of 1M sodium hydroxide at room temperature under argon and the solution was stirred for 2.5 hours, then heated at 55° C. for 16 hours. After cooling and lyophilization, the crude product was purified by chromatography on a 2.5×12 cm column of HP-20 loaded with water. The column was eluted with 150 mL water followed by 350 mL of 10:90 acetonitrile:water. Appropriate fractions were combined, the acetonitrile was evaporated, and the aqueous solution was lyophilized to obtain (30.5 mg, 40%) of the title compound as a white lyophilate.

TLC Silica gel (6:3:1 n-propanol:concentrated ammonia:water) Rf=0.43.

Analysis Calculated for $C_{18}H_{29}O_5P.Na_3$.1.1 water (MW= 445.39): Calculated: C, 48.54; H, 7.09. Found: C, 48.57; H, 6.94.

EXAMPLE 4

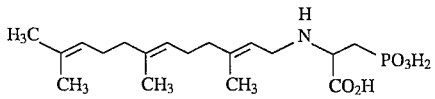

(E,E)-3-[(Dihydroxyphosphinyl)-2-(3,7,11-trimethyl-2,6,10-dodecatrienyl)amino]propanoic acid, disodium salt A. N-Trifluoroacetyl-(E,E)-3-[(dihydroxyphosphinyl)- 2-(3,7,11-trimethyl-2,6,10 -dodecatrienyl)amino]propanoic acid, triethyl ester A solution of 620 mg (1.78 mmol) of N-trifluoromethylcarbonyl-phosphonomethyl glycine, triethyl ester and 655 mg (2.30 mmol) of farnesyl bromide in 6 mL of dry DMF was treated with 0.98 g (7.12 mmol) of anhydrous potassium carbonate. The mixture was stirred for 3 hours, diluted with ether, washed with four portions of 1:1 water:brine followed by brine, dried (magnesium sulfate) and evaporated to provide 1.02 g of an oil. Flash chromatography on 70 g of silica gel packed in 30:70 ether:petroleum ether, eluted with 50:50 ether:petroleum ether, followed by 60:40 ether:petroleum ether provided 104 mg (10%) of slightly impure Compound A and 584 mg (60%) of pure Compound A as a colorless oil.

TLC Silica gel (ethyl ether) Rf=0.43.
B. (E,E)-3-[(Dihydroxyphosphinyl)-2-(3,7,11 -trimethyl-2,6,10-dodecatrienyl)amino]propanoic acid, disodium salt To a solution of 419 mg (0.758 mmol) of Compound A in 3 mL of dichloromethane under argon was added 0.2 mL (1.52 mmol) of 2,4,6-collidine followed by 0.4 mL (3.30 mmol) of bromotrimethylsilane. After 7 hours, an additional 0.1 mL (0.76 mmol) of 2,4,6-collidine and 0.1 mL (0.76 mmol) of bromotrimethylsilane was added. After 18 hours, the solution was evaporated, dissolved in benzene, evaporated again and pumped at high vacuum. The residue was dissolved in 8 mL of 1M sodium hydroxide and stirred for 2 hours at room temperature, followed by 17 hours at 58° C. The aqueous phase was lyophilized to give 690 mg of a pink residue. The crude material was purified by chromatography on a column of HP-20 (2.5×22 cm), packed and eluted with water, followed by the gradient addition of 75:25 acetonitrile:water to a reservoir of pure water. The pure fractions were combined, the acetonitrile was evaporated and the residue was freeze-dried to provide 286 mg (90%) of the title compound as a white lyophilate, which was dried further at high vacuum.

TLC Silica gel (7:2:1 n-propanol:concentrated ammonia:water) Rf=0.26.

Analysis Calculated for $C_{18}H_{30}NO_5P$: Calculated: C, 45.94; H, 7.69; N, 3.36; P, 6.58. Found: C, 45.97; H, 6.59; N, 2.97; P, 6.80.

EXAMPLE 5

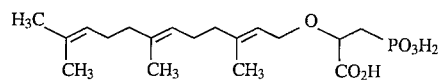

(E,E)-3-(Dihydroxyphosphinyl)-2-[(3,7,11-trimethyl-2,6,10-dodecatrienyl)oxy]propanoic acid, trisodium salt A. (E,E)-2-[(3,7,11-Trimethyl-2,6,10 -dodecatrienyl)oxy] malonic acid, dimethyl ester To a mixture of 4.00 g (18.0 mmol) of farnesol and 20 mg (2 mol %) of rhodium acetate dimer in 15 mL of refluxing benzene under argon, was added 3.14 g (19.8 mmol) of dimethyl diazomalonate in 5 mL of dry benzene over two hours. The amber solution was allowed to cool, and the solvent was evaporated. Purification by flash chromatography on 500 g silica, eluted with 7.5:92.5 ethyl acetate:petroleum ether, provided 4.64 g (73%) of Compound A as a colorless oil.

TLC Silica gel (1:9 ethyl acetate:hexanes) Rf=0.21.
B. 2-(Dimethylaminomethyl)-(E,E)-2-[(3,7,11-trimethyl-2,6,10-dodecatrienyl)oxy]malonic acid, dimethyl ester To a mixture of 2.50 g (7.1 mmol) of Compound A and 1.97 g (10.7 mmol) of N,N-dimethylmethyleneammonium iodide in 100 mL of dichloromethane under argon was added 1.60 mL (11.5 mmol) of triethylamine. The resulting yellow solution was stirred for 2.5 hours and washed with 25 mL of sodium carbonate, and the aqueous layer was extracted with 40 mL of dichloromethane. The organic phase was dried over magnesium sulfate and evaporated. The residue was triturated with ethyl ether, solids were filtered off, and the solvent was evaporated to yield 3.80 g of crude product. Flash chromatography on 300 g of silica, eluted with 1:9 ethyl acetate:petroleum ether, provided 2.37 g (81%) of Compound B.

TLC Silica gel (2:8 ethyl acetate:hexanes) Rf=0.10.
C. (E,E)-2-[(3,7,11-Trimethyl-2,6,10-dodecatrienyl)oxy] propenoic acid, methyl ester A solution of 2.25 g (5.5 mmol) of Compound B in 20 ml of ethyl ether under argon was treated with 6.85 mL (110 mmol) of iodomethane, capped, and stirred for 24 hours. Filtration provided 2.76 g (91%) of the amine methiodide of Compound B as white platelets. To a solution of 2.6 g (4.71 mmol) of this methiodide salt in 50 mL of methanol at 0° C. under argon, 50.9 mL (5.09 mmol) of cold 0.1M sodium hydroxide was added over 30 minutes. After stirring for three hours at 0° C., the methanol was removed and the remaining aqueous solution was extracted with five 50 mL portions of dichloromethane. The combined organic layers were washed with brine, dried over magnesium sulfate and evaporated. The residue was dissolved in 13 mL of methanol at 0° C. under argon, treated over 15 minutes with 13 mL (1.3 mmol) of 0.1M sodium hydroxide, and stirred for three hours at 0° C. and one hour at room temperature. The methanol was removed and the aqueous solution was extracted with five 50 mL portions of dichloromethane. The combined organic layers were washed with brine, dried over magnesium sulfate and evaporated to afford 1.27 g of a clear yellow oil. Flash chromatography on 50 g of silica, eluted with 5:95 ethyl acetate:petroleum ether, provided 1.12 g of Compound C as a colorless oil.

TLC Silica gel (5:95 ethyl acetate:hexanes) Rf=0.13.

D. (E,E)-3-(Dihydroxyphosphinyl)-2-[(3,7,11 -trimethyl-2,6,10-dodecatrienyl)oxy]propanoic acid, triethyl ester To a solution of 434 mg (1.42 mmol) of Compound C in 0.85 mL of ethanol under argon was added 75 µL (0.15 mmol) of 2M sodium ethylate. After two hours, an additional 75 µL of 2M sodium ethylate and 4 mL of ethanol were added. The mixture was stirred for two hours, the ethanol was removed and the residue was dissolved in 50 mL of ethyl ether. The organic solution was washed with three 10 mL portions of water and 10 mL of brine, dried over magnesium sulfate and evaporated to yield 327 mg of crude product. Flash chromatography on 35 g of silica of this crude product combined with 78 mg of crude product from a previous reaction provided 330 mg (59%) of the ethyl ester as a colorless oil.

A solution of 330 mg (1.03 mmol) of the ethyl ester and 530 µL (4.12 mmol) of diethyl phosphite in 1.5 mL of tetrahydrofuran under argon was treated with 520 µL (0.26 mmol) of a 0.5M solution of potassium bis(trimethylsilyl)amide in toluene and stirred for 22 hours. The reaction was quenched with saturated ammonium chloride and diluted with 20 mL of ethyl ether. The organic phase was washed with three 5 mL portions of water and 5 mL portions of brine, dried over magnesium sulfate and evaporated to give 513 mg of crude product as a colorless oil. Flash chromatography on 60 g of silica, eluted with 3:7 ethyl acetate: petroleum ether, provided 367 mg (78%) of Compound D as a colorless oil.

TLC Silica gel (1:1 ethyl acetate:hexanes) Rf=0.16.

E. (E,E)-3-(Dihydroxyphosphinyl)-2-[(3,7,11 -trimethyl-2,6,10-dodecatrienyl)oxy]propanoic acid, trisodium salt A solution of 363 mg (0.79 mmol) of Compound D and 160 µL (1.19 mmol) of collidine in 2.0 mL of dichloromethane under argon was treated with 315 µL (2.37 mmol) of bromotrimethylsilane, and the resultant white suspension was stirred for 5.5 hours. The solvent was evaporated, the residue was twice evaporated with benzene, and the final residue was pump-dried. After dissolving in 4.75 mL (4.75 mmol) of 1M sodium hydroxide, the mixture was stirred for 16 hours and lyophilized. Purification was performed by chromatography on a 2.5×15 cm column of HP-20 packed with water. The column was eluted with 215 mL of water followed by a gradient created by the gradual addition of 400 mL of a 75:25 acetonitrile:water mixture into 400 mL of water. Appropriate fractions were combined, evaporated, lyophilized and pump-dried to provide 227 mg (65%) of the title compound as a white lyophilate.

TLC Silica gel (6:3:1 n-propanol:ammonia:water) Rf=0.42.

Analysis Calculated for $C_{18}H_{28.5}O_5P\cdot Na_{2.5}\cdot 2.6\%$ water (MW=440.539): Calculated: C, 49.08; H, 6.53; P, 7.03. Found: C, 49.36; H, 6.86; P, 6.77.

EXAMPLE 6

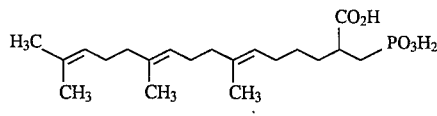

(E,E)-2-[(Dihydroxyphosphinyl)methyl]-7,11,15-trimethyl-6,10,14-hexadecatrienoic acid, trisodium salt The compound of Example 6 was prepared from 1-iodo-5,9,13-trimethyl-4,8,12-tetradecatriene and phosphonomethylmalonate, triethyl ester as described in the preparation of Example 3.

Analysis Calculated for $C_{20}H_{32}O_5P\cdot Na_3\cdot 0.49$ equiv. water (MW=461.15): Calculated: C, 52.09; Hi 7.21; P, 6.72. Found: C, 52.10; H, 7.58; P, 6.77.

EXAMPLE 7

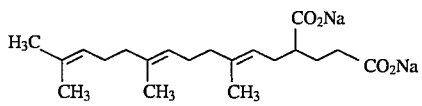

(E,E)-2-(3,7,11-Trimethyl-2,6,10-dodecatrienyl) pentanedioic acid, disodium salt A. 2-Ethoxycarbonyl-5,9,13-trimethyl-4,8,12-teradecatrienoic acid, ethyl ester Sodium hydride (60% in oil, 160 mg, 4.0 mmol) was added to a solution of diethyl malonate (0.6 mL, 4.0 mmol) under argon. After the effervescence subsided, farnesyl bromide (1.14 g) was added. After 18 hours, the mixture was cooled to 0° C. and methanol (0.2 mL) followed by saturated ammonium chloride (5 mL) was added. The mixture was extracted with hexanes (2×5 mL) and the combined organic layer was dried (magnesium sulfate), filtered and concentrated. The residue was purified by silica gel flash column chromatography eluted with 3% ethyl acetate in hexanes to afford Compound A (pure 0.64 g, slightly impure 0.81 g, 92% yield).

TLC: $R_f$ 0.4 (10% ethyl acetate in hexanes, PMA).

B. 4,4-(bis-(Ethoxycarbonyl))-7,11,15- trimethyl-6,10,14-hexadecatrienoic acid, ethyl ester To a solution of potassium-t-butoxide (42 mg, 0.4 mmol) in t-butanol (4 mL) under argon was added Compound A (364 mg, 1.0 mmol). After 10 minutes, a solution of ethyl acrylate (0.16 mL, 1.5 mmol) in tetrahydrofuran (3 mL) was added. After 4 hours, the mixture was poured into saturated aqueous ammonium chloride (10 mL) and extracted with ethyl acetate (2×5 mL). The organic layers were combined, washed with brine (10 mL), dried (magnesium sulfate), filtered and concentrated. The residue was purified on silica gel (25×200 mm), eluting with 5% ethyl acetate in hexanes to afford Compound B (315 mg, 66%).

TLC: $R_f$ 0.4 (5% ethyl acetate in hexanes, PMA).

C. (E,E)-2-Ethoxycarbonyl-2-(3,7,11-trimethyl-2,6,10-dodecatrienyl)pentanedioic acid A solution of sodium hydroxide (200 mg, 5.0 mmol) in water (1.5 mL) was added dropwise to a solution of Compound B (238 mg, 0.5 mmol) in ethanol (1.5 mL). After 18 hours, the solvents were removed, and the residue was dissolved in water (8 mL) and washed with ethyl acetate (2×10 mL). The aqueous solution was acidified with 10% potassium bisulfate (DH=3) in the presence of ethyl acetate (20 mL). After the two layers were separated, the aqueous solution was extracted with ethyl acetate (10 mL) and the combined organic extracts were dried (magnesium sulfate), filtered and concentrated to give Compound C (140 mg, 63%).

TLC: $R_f$ 0.51 (ethyl acetate:hexanes:acetic acid, 8:2:0.02, PMA).

D. 4-(Ethoxycarbonyl)-7,11,15-trimethyl-6,10,14-hexadecatrienoic acid

A solution of Compound C (180 mg, 0.44 mmol) in xylene (3 mL) was heated at reflux. After 12 hours, the mixture was cooled and the volatiles were removed under vacuum. The residue was purified on silica gel (25×150 mm) eluting with 0.5% acetic acid in ethyl acetate to give compound D (150 mg, 93%).

TLC: $R_f$ 0.6 (0.5% acetic acid in ethyl acetate, PMA).

E. (E,E)-2-(3,7,11-Trimethyl-2,6,10-dodecatrienyl)pentanediolic acid, disodium salt Sodium hydroxide (32 mg, 0.8 mmol) was added to a solution of Compound D (50 mg, 0.13 mmol) in methanol (0.8 mL). After 15 hours, the volatiles were removed under vacuum, and the residue was purified on CHP 20P column (11×150 mm) eluting with methanol in water (0% to 40%). Appropriate fractions were combined and lyophilized to give the title compound.

mp: 210° C. dec. TLC: $R_f$ 0.38 (ethyl acetate:hexanes:acetic acid, 79.5:20:0.5, visualized by PMA) Analysis Calculated for $C_{20}H_{30}O_4Na_2 \cdot 1.19 \ H_2O$: Calculated: C, 61.65; H, 8.02. Found: C, 61.65; H, 7.83.

EXAMPLE 8

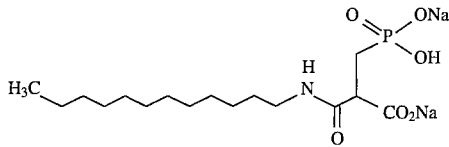

3-(Dodecylamino)-3-oxo-2-(phosphonomethyl)propanoic acid, disodium salt

A. 3-(Dodecylamino)-3-oxo-2-(phosphonomethyl)propanoic acid, triethyl ester 1,1'-Carbonyldiimidazole (0.287 g, 1.77 mmol) was added to a solution of O,O-diethylphosphonomethylmalonate monoethyl ester (0.5 g, 1.77 mmol) in tetrahydrofuran (3 ml) and the resultant mixture was stirred for 15 minutes at 0° C. and 1 hour at 20° C. After cooling to 0° C., dodecylamine (0.33 g, 1.77 mmol) was added and the mixture stirred for 16 hours. The reaction was quenched with hydrochloric acid (1N, 50 ml) and extracted with ethyl acetate (3×50 ml). The combined organic extracts were washed with sodium carbonate (10%, 50 ml), dried (magnesium sulfate), filtered and concentrated under vacuum. Flash chromatography (eluting with 2:1 hexane/acetone) afforded Compound A (0.48 g, 61%).

TLC: $R_f$=0.86 (4:1 acetone/hexane, visualization by $I_2$/PMA).

B. 3-(Dodecylamino)-3-oxo-2-(phosphonomethyl)propanoic acid, disodium salt

Bis(trimethylsilyl)trifluoroacetamide (0.537 ml, 2.02 mmol) was added to a solution of Compound A (0.2 g, 0.50 mmol) in dichloromethane (5 ml) and stirred for 1 hour at room temperature. Bromotrimethylsilane (0.13 ml, 0.99 mmol) was added and the mixture was stirred for 16 hours and concentrated under vacuum. The residue was dissolved in methanol (5 ml) and sodium hydroxide (1N, 3.59 ml, 3.59 mmol), stirred for 15 minutes and concentrated under vacuum. The residue was purified by CHP-20P gel (eluting sequentially with water (500 ml) and acetonitrile (30%, 500 ml)) to afford the title compound (0.07 g, 36%), mp: decomposition starting 245° C.

TLC: $R_f$=0.82 (6:3:1 n-propanol/ammonium hydroxide/water, visualization by $I_2$/anisaldehyde).

Analysis Calculated for $C_{16}H_{30}NO_6PNa_2$: Calculated: C, 44.97; H, 7.55; N, 3.28. Found: C, 44.99; H, 7.62; N, 3.35.

EXAMPLE 9

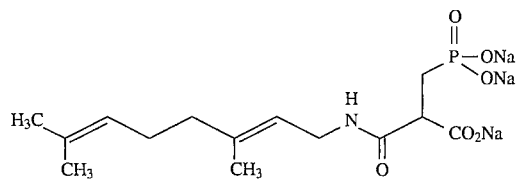

(E)-3-[(3,7-Dimethyl-2,6-octenyl)amino]-3-oxo-2-(phosphonomethyl)-propanoic acid, trisodium salt A. N-(3,7-Dimethyl-2,6-octenyl)-phthalimide Potassium phthalimide (2.34 g, 12.7 mmol) was added to a solution of geranyl bromide (2.5 g, 11.5 mmol) in DMF (30 ml) and the mixture was stirred for 18 hours. The reaction was quenched with lithium chloride (10%, 50 ml) and extracted with diethyl ether (3×50 ml). The combined organic extracts were washed with lithium chloride (3×50 ml), dried (magnesium sulfate), filtered and concentrated under vacuum. Flash chromatography (eluting with 20:1 hexane/ethyl acetate) afforded Compound A (2.3 g, 71%), mp 58°–60° C.

B. 3,7-Dimethyl-2,6-octenylamine, hydrochloride

A solution of methyl hydrazine (2.16 ml, 40.6 mmol) and Compound A (2.3 g, 8.13 mmol) in ethanol (15 ml) was stirred for 16 hours and heated at reflux for 3 hours. Additional methyl hydrazine (2.16 ml, 40.6 mmol) was added and the mixture was stirred for 1 hour and cooled to room temperature. Sodium hydroxide (1N, 8.1 ml) was added, and the mixture was stirred for 5 minutes and concentrated. The residue was dissolved in sodium hydroxide (1N, 50 ml) and extracted with diethyl ether (3×50 ml), and the combined organic extracts were dried (magnesium sulfate), filtered and concentrated. The residue was dissolved in diethyl ether (10 ml) and cooled to 0° C., and anhydrous hydrochloric acid in dioxane (3M, 10 ml) was added. The precipitated material was filtered, washed with petroleum ether and dried under vacuum to afford Compound B (1.2 g, 78%), mp 142°–145° C.

C. (E)-3-[(3,7-Dimethyl-2,6-octenyl)amino]-3-oxo-2-(phosphonomethyl)-propanoic acid, triethyl ester Compound C was prepared from Compound B and O,O-diethyl-phosphonomethylmalonate monoethyl ester as described for Compound A of Example 8, using diisopropylethyl amine as a base. Chromatography with 19:1 chloroform/methanol afforded compound C (0.256 g, 58%).

TLC: $R_f$=0.75 (9:1:0.05 chloroform/methanol/acetic acid, visualization by PMA).

D. (E)-3-[(3,7-Dimethyl-2,6-octenyl)amino]-3-oxo-2-(phosphonomethyl)-propanoic acid, trisodium salt The title compound was prepared from Compound C under conditions described for the preparation of the compound of Example 8.

mp: decomposition above 250° C.

TLC: $R_f=0.54$ (6:3:1 n-propanol/ammonium hydroxide/water, visualization by anisaldehyde) Analysis Calculated for $C_{14}H_{21}O_6NPNa_3 \cdot 0.25\ H_2O$: Calculated: C, 41.64; H, 5.37; N, 3.47. Found: C, 41.87; H, 5.75; N; 3.33.

EXAMPLE 10

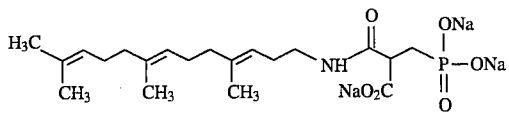

(E,E)-3-Oxo-2-(phosphonomethyl)-3-[(4,8,12-trimethyl-3,7,11-tridecatrienyl)-amino]-propanoic acid, trisodium salt The title compound was prepared from 1-(4,8,12-trimethyl-3,7,11-tridecatrienyl)-amine and O,O-diethyl-phosphonomethylmalonate monoethyl ester as described for the preparation of the compound of Example 8. Purification was accomplished on SP-207 gel, eluting sequentially with water and acetonitrile.

mp: decomposition above 210° C. TLC: $R_f=0.44$ (6:3:1 n-propanol/ammonium hydroxide/water, visualization by anisaldehyde). Analysis Calculated for $C_{20}H_{31}NPO_6Na_3 \cdot 0.64\ H_2O$: Calculated: C, 48.74; H, 6.60; N, 2.84. Found: C, 49.02; H, 6.95; N, 2.68.

EXAMPLE 11

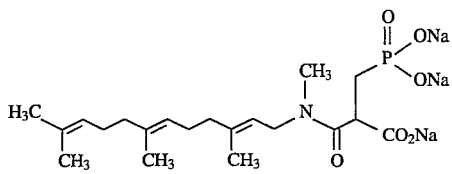

(E,E)-3-[Methyl-(3,7,11-trimethyl-2,6,10-dodecatrienyl)amino]3-oxo-2-(phosphonomethyl)propanoic acid, trisodium salt A. N-[Methyl(3,7,11-trimethyl-2,6,10-dodecatrienyl)]-N-methyl-4-methylbenzenesulfonamide Triphenylphosphine (3 5.4 g, 135 mmol) was added to a solution of N-methyl-p-toluenesulfonamide (20.9 g, 112) in tetrahydrofuran (150 ml). To the stirring mixture was added farnesol (10 g, 5.0 mmol), and the reaction was cooled to 0° C. Diethylazodicarboxylate (17.7 ml, 112 mmol) was added dropwise and the reaction was warmed to room temperature and stirred for 3 hours. The mixture was concentrated under vacuum, the residue passed through a silica gel plug (eluting with 1:1 ethyl acetate/hexane) and the eluent concentrated under vacuum. Flash chromatography (eluting with 8:1 hexane/ethyl acetate) afforded Compound A (14.5 g, 83%).

TLC: $R_f=0.56$ (4:1 hexane/ethyl acetate, visualization by PMA).

B. Methyl-(3,7,11-trimethyl-2,6,10-dodecatrienyl)-amine

Sodium (0.22 g, 9.6 mmol) was added to a solution of naphthalene (2.1 g, 9.6 mmol) in 1,2 dimethoxyethane (12.8 ml) and stirred for 1.5 hours. A solution of Compound A (0.83 mg, 2.13 mmol) in 1,2 dimethoxyethane (1 ml) was added in one portion and stirring was continued for 1 hour. The reaction was quenched with water (2 ml) followed by sodium bicarbonate (10%, 40 ml) and extracted with diethyl ether (3×50 ml), and the combined organic extracts were dried (magnesium sulfate), filtered and concentrated under vacuum to afford Compound B, which was used immediately without purification.

TLC: $R_f=0.19$ (9:1:0.05 chloroform/methanol/acetic acid, visualization by PMA).

C. (E,E)-3-[Methyl-(3,7,11-trimethyl-2,6,10-dodecatrienyl)amino]3-oxo-2-(phosphonomethyl)-propanoic acid, triethyl ester Compound C was prepared from Compound B and O,O-diethyl-phosphonomethylmalonate monoethyl ester as described for Compound A from Example 8.

TLC: $R_f=0.57$ (1:1 hexane/acetone, visualization by PMA).

D. (E,E)-3-[Methyl-(3,7,11-trimethyl-2,6,10-dodecatrienyl)amino]3-oxo-2-(phosphonomethyl)propanoic acid, trisodium salt The title compound was prepared from Compound D under conditions described for the preparation of the compound of Example 8. Purification was accomplished on SP-207 gel, eluting sequentially with water and acetonitrile.

mp: decomposition above 200° C. TLC: $R_f=0.50$ (6:3:1 n-propanol/ammonium hydroxide/water, visualization by PMA) Analysis Calculated for $C_{20}H_{31}NO_6PNa_3 \cdot 0.68\ H_2O$: Calculated: C, 48.66; H, 6.61; N, 2.84. Found: C, 48.83; H, 6.37; N, 2.67.

EXAMPLE 12

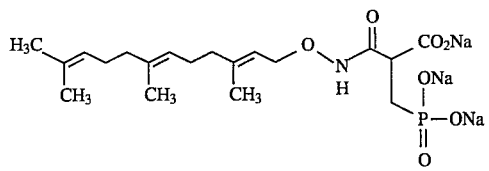

(E,E)-3-Oxo-2-(phosphonomethyl)-3-[[(3,7,11-trimethyl-2,6,10-dodecatrienyl)oxy]amino]propanoic acid The title compound was prepared from 3,7,11-trimethyl-2,6,10-dodecatrienyl)oxy]amine and O,O-diethyl-phosphonomethylmalonate monoethyl ester as described for the preparation of the compound of Example 8. Chromatography on SP-207 gel (eluting sequentially with water and acetonitrile) afforded the title compound.

mp: decomposition above 205° C. TLC: $R_f=0.49$ (6:3:1 n-propanol/ammonium hydroxide/water, visualization by PMA). Analysis Calculated for $C_{19}H_{29}NO_7PNa_3 \cdot 1.0\ H_2O$: Calculatedd: C, 45.51; H, 6.23; N, 2.79. Found: C, 45.63; H, 6.54; N, 2.63.

EXAMPLE 13

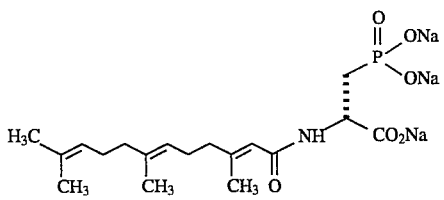

[S-(E,E)]-3-Phosphono-2-[(3,7,11-trimethyl-1-oxo-2,6,
10-dodecatrienyl)amino]-propanoic acid, trisodium salt A. [S-(E,E)]-3-Phosphono-2-[(3,7,11-trimethyl-1-oxo-2,6,
10-dodecatrienyl)amino]-propanoic acid trimethyl ester Benzotriazol-1-yloxy-tris(dimethylamino)phosphonium hexafluorophosphate reagent (0.66 g, 1.5 mmol) was added to a solution of 3,7,11-trimethyl-2,6,10-dodecatrienoic acid and S-2-amino-3-phosphono-propionic acid, trimethyl ester hydrochloride (0.37 g, 1.5 mmol) in acetonitrile (5 ml) and DMF (1.7 ml). Diisopropylethylamine (0.52 ml, 3.0 mmol) was added and the mixture was stirred for 72 hours. The reaction was quenched with hydrochloric acid (1N, 50 ml) and extracted with ethyl acetate (4×50 ml). The combined organic extracts were washed sequentially with sodium carbonate (10%, 50 ml) and lithium chloride (10%, 2×100 ml), dried, filtered and concentrated under vacuum. Flash chromatography (4:1 hexane/acetone) afforded Compound A (0.27 g, 42%).

TLC: $R_f$=0.52 (1:1 hexane/acetone, visualization by PMA).

$[\alpha]_D$=–15.2° (c=1.21, trichloromethane).

B. [S-(E,E)]-3-Phosphono-2-[(3,7,11-trimethyl-1-oxo-2,6,
10-dodecatrienyl)amino]-propanoic acid, trisodium salt Bis(trimethylsilyl)trifluoroacetamide (0.61 ml, 2.3 mmol) was added to a solution of compound A (0.16 g, 0.38 mmol) in dichloromethane (2 ml) and stirred for 1 hour. Bromotrimethylsilane (0.12 ml, 0.96 mmol) was added and the mixture was stirred for 2 hours. The mixture was concentrated under vacuum, and the residue was dissolved in methanol (2 ml) and sodium hydroxide (1N, 3.5 ml), stirred for 15 minutes and concentrated under vacuum. The residue was purified by SP-207 gel (eluting sequentially with water (250 ml) and 70% aqueous methanol (250 ml)) and the appropriate fractions were concentrated under vacuum. The residue was dissolved in water (15 ml), millipore filtered and lyophilized to afford the title compound (0.12 g, 69%), mp: decomposition above 210° C.

TLC: $R_f$=0.53 (6:3:1 n-propanol/ammonium hydroxide/water, visualization by UV). $[\alpha]_D$=–4.5° (c=0.92, methanol). Analysis Calculated for $C_{18}H_{27}NO_6PNa_3$: Calculated: C, 47.69; H, 6.00; N, 3.09. Found: C, 48.04; H, 6.38; N, 3.03.

EXAMPLE 14

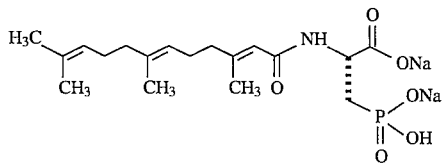

[R-(E,E)]-3-Phosphono-2-[(3,7,11-trimethyl-1-oxo-2,
6,10-dodecatrienyl)amino]-propanoic acid, disodium salt The title compound was prepared from 3,7,11-trimethyl-2,6,10-dodecatrienoic acid and R-2-amino-3-phosphono-propionic acid, trimethyl ester hydrochloride as described for Compound A of Example 13.

mp: decomposition above 210° C. TLC: $R_f$=0.52 (6:3:1 n-propanol/ammonium hydroxide/water, visualization by UV). $[\alpha]_D$=+4.3° (c=0.91, methanol). Analysis Calculated for $C_{18}H_{28}NO_6PNa_2$: Calculated: C, 49.09; H, 6.64; N, 3.18. Found: C, 49.08; H, 6.44; N, 3.00.

EXAMPLE 15

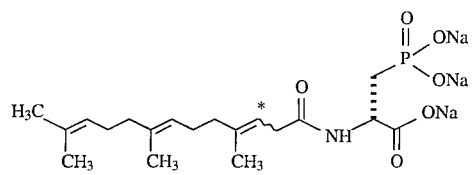

[S-(E,E)]-3-Phosphono-2-[(4,8,12-trimethyl-1-oxo-3,
7,11-dodecatrienyl)amino])-propanoic acid,
trisodium salt, 33% (Z,E) isomer The title compound was prepared in 2 steps from 4,8,12-trimethyl-3,7,11-dodecatrienoic acid, 33% (Z,E) isomer and S-2-amino-3-phosphonopropionic acid, trimethyl ester hydrochloride as described for Compound A of Example 13. Chromatography on CHP-20P gel (eluting sequentially with water and 20% aqueous methanol) afforded the title compound, mp: decomposition above 175° C.

TLC: $R_f$=0.35 (6:3:1 n-propanol/ammonium hydroxide/water, visualization by anisaldehyde). $[\alpha]_D$=–3.5° (c=0.4, methanol).

Analysis Calculated for $C_{19}H_{29}NO_6PNa_3$-2.05 $H_2O$: Calculated: C, 45.25; H, 6.62; N, 2.78. Found: C, 45.56; H, 6.77; N, 2.47.

EXAMPLE 16

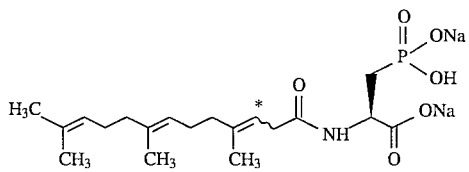

[R-(E,E)]-3-Phosphono-2-[(4,8,12-trimethyl-1-oxo-3,
7,11-dodecatrienyl)amino]-propanoic acid,
trisodium salt, 33% (Z,E) isomer The title compound was prepared in 2 steps from 4,8,12-trimethyl-3,7,11-dodecatrienoic acid, 33% (Z,E) isomer and R-2-amino-3-phosphonopropionic acid, trimethyl ester hydrochloride as described for Compound A of Example 13. Chromatography on CHP-20P gel (eluting sequentially with water and 50% aqueous methanol) afforded the title compound, mp: decomposition above 215° C.

TLC: $R_f$=0.58 (6:3:1 n-propanol/ammonium hydroxide/water, visualization by anisaldehyde). $[\alpha]_D$=+17.5° (c=0.4, methanol). Analysis Calculated for $C_{19}H_{30}NO_6PNa_2$-1.4 $H_2O$: Calculated: C, 48.49; H, 7.02; N, 2.98. Found: C, 48.49; H, 6.96; N, 2.92.

EXAMPLE 17

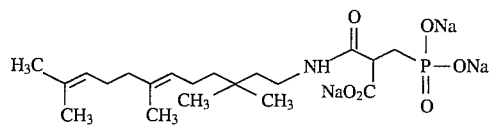

(E)-2-(Phosphonomethyl)-3-oxo-3-[(3,3,7,11
-tetramethyl-6,10-dodecadienyl)amino]-propanoic acid,
trisodium salt A. 1-(3,3,7,11-Tetramethyl-6,10-dodecadienyl)amine Ammonium acetate (1.62 g, 21.0 mmol) was added to a solution of 3,3,7,11-tetramethyl-6,10-dodecadien-1-al (0.5 g, 2.1 mmol) and 4 Å powdered molecular sieves (0.50 g) in methanol (8 ml). Sodium cyanoborohydride (0.133 g, 2.1 mmol) was added and the mixture was stirred for 16 hours. The reaction was quenched with water (1 ml), stirred 0.5 hours and filtered through Celite® (eluting with methanol), and the filtrate was concentrated under vacuum. The residue was dissolved in dichloromethane (10 ml), dried (magnesium sulfate), filtered and concentrated under vacuum. Flash chromatography (eluting with 4:1 hexane/ethyl acetate, then 5:1 trichloromethane/methanol) afforded Compound A (0.137 g, 27%).

TLC: $R_f$=0.13 (9:1 chloroform/methanol, visualization by PMA).

B. (E)-2-(Phosphonomethyl)-3-oxo-3-[(3,3,7,11 -tetramethyl-6,10-dodecadienyl)amino]-propanoic acid, triethyl ester Compound B was prepared from Compound A and (diethyl phosphonomethyl)malonic acid, monoethyl ester as described for Compound A of Example 13.

TLC: $R_f$=0.53 (1:1 hexane/acetone, visualization by PMA).

C. (E)-2-(Phosphonomethyl)-3-oxo-3-[(3,3,7,11 -tetramethyl-6,10-dodecadienyl)amino]-propanoic acid, trisodium salt The title compound was prepared from Compound B as described for Compound B of Example 13, with chromatography on CHP-20P gel (eluting sequentially with water and 50% aqueous acetonitrile).

mp: decomposition above 220° C. TLC: $R_f$=0.32 (6:3:1 n-propanol/ammonium hydroxide/water, visualization by anisaldehyde). Analysis Calculated for $C_{20}H_{33.3}NO_6PNa_{2.7}$-0.15 $H_2O$: Calculated: C, 50.09; H, 7.06; N, 2.92. Found: C, 50.01; H, 7.40; N, 3.09.

EXAMPLE 18

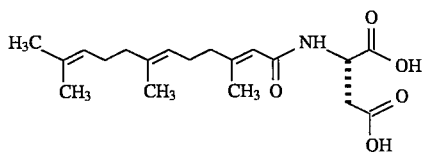

(E,E)-N-[(3,7,11-Trimethyl-1-oxo-2,6,10
-dodecatrienyl)]-L-aspartic acid, disodium salt A. (E,E)-N-[(3,7,11-Trimethyl-1-oxo-2,6,10 -dodecatrienyl)]-L-aspartic acid, dimethyl ester Compound A was prepared from L-aspartic acid dimethyl ester hydrochloride and 3,7,11-trimethyl-2,6,10-dodecatrienoic acid as described for Compound A from Example 13.

B. (E,E)-N-[(3,7,11-Trimethyl-1-oxo-2,6,10 -dodecatrienyl)]-L-aspartic acid, disodium salt Sodium hydroxide (1N, 1.39 ml, 1.39 mmol) was added to a solution of Compound A (0.25 g, 0.66 mmol) in methanol (5 ml) and stirred for 16 hours. The reaction was concentrated under vacuum, dissolved in water (5 ml) and purified through a CHP-20P gel column (eluting sequentially with water (125 ml) and 10% aqueous acetonitrile (250 ml)). The appropriate fractions were combined, concentrated under vacuum, millipore filtered and lyophilized to afford the title compound (0.205 g, 79%), mp: decomposition above 240° C.

TLC: $R_f$=0.57 [6:3:1 n-propanol/ammonium hydroxide/water, visualization by PMA]. $[\alpha]_D$+24.3° [c=1.17, methanol]. Analysis Calculated for $C_{19}H_{27}NO_5Na_2$-0.23 $H_2O$: Calculated: C, 57.11; H, 6.93; N, 3.50. Found: C, 57.20; H, 7.17; N, 3.41.

EXAMPLE 19

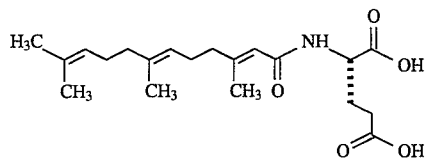

(E,E)-N-[(3,7,11-Trimethyl-1-oxo-2,6,10
-dodecatrienyl)]-L-glutamic acid, disodium salt The title compound was prepared from L-glutamic acid dimethyl ester hydrochloride and 3,7,11-trimethyl-2,6,10-dodecatrienoic acid as described for the compound of Example 18.

mp: decomposition above 240° C. TLC: $R_f$=0.68 [6:3:1 n-propanol/ammonium hydroxide/water, visualization by PMA]. $[\alpha]_D$+14.8° [c=1.21, methanol]. Analysis Calculated for $C_{20}H_{29}NO_5Na_2$-0.42 $H_2O$: Calculated: C, 57.61; H, 7.21; N, 3.36. Found: C, 57.57; H, 7.17; N, 3.40.

EXAMPLE 20

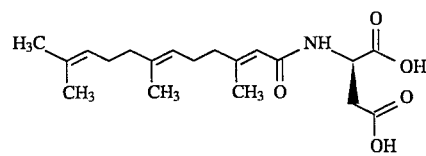

(E,E)-N-[(3,7,11-Trimethyl-1-oxo-2,6,10
-dedecatrienyl)]-D-aspartic acid, disodium salt The title compound was prepared from D-aspartic acid dimethyl ester hydrochloride and 3,7,11-trimethyl-2,6,10-dodecatrienoic acid as described for the compound of Example 18.

mp: decomposition above 240° C. TLC: $R_f$=0.57 [6:3:1 n-propanol/ammonium hydroxide/water, visualization by PMA]. $[\alpha]_D$-26.01° [c=1.43, methanol]. Analysis Calculated for $C_{19}H_{27}NO_5Na_2$-0.21 $H_2O$: Calculated: C, 57.18; H, 6.92; N, 3.51. Found: C, 57.17; H, 6.51; N, 3.52.

EXAMPLE 21

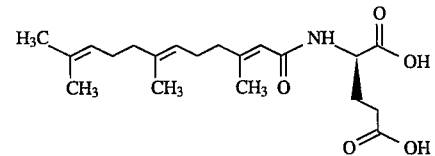

(E,E)-N-[(3,7,11-Trimethyl-1-oxo-2,6,10-dodecatrienyl)]-D-glutamic acid, disodium salt The title compound was prepared from D-glutamic acid dimethyl ester hydrochloride and 3,7,11-trimethyl-2,6,10-dodecatrienoic acid as described for the compound of Example 18.

mp: decomposition above 200° C. TLC: $R_f=0.79$ [6:3:1 n-propanol/ammonium hydroxide/water, visualization by PMA][α]$_D$–14.9° [c=1.14, methanol]. Analysis Calculated for $C_{20}H_{29}NO_5Na_2$·0.51 $H_2O$: Calculated: C, 57.39; H, 7.23; N, 3.35. Found: C, 57.12; H, 7.11; N, 3.62.

What is claimed is:

1. A compound of the formula

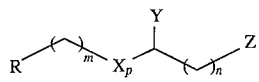

or an enantiomer, diastereomer, pharmaceutically acceptable salt, prodrug or solvate thereof, wherein:

X is —NR$^1$C(O)— or —C(O)NR$^1$—;

one of Y and Z is —CO$_2$R$^2$ and the other is —P(O)(OR$^2$)(OR$^3$);

R is alkyl, substituted alkyl, alkenyl, substituted alkenyl, alkenylene or aryl;

R$^1$, R$^2$ and R$^3$ are each independently hydrogen, alkyl, aryl or aralkyl;

m is 0 or an integer from 1 to 5;

n is an integer from 1 to 5; and p is 0 or 1.

2. A compound of claim 1, wherein X is —NR$^1$C(O)— or —C(O)NR$^1$— when p is 1.

3. A compound of claim 1, wherein X is —NHC(O)—, —NCH$_3$C(O)— or —C(O)NH— when p is 1.

4. A compound of claim 1, wherein p is 0.

5. A compound of claim 1, wherein Y is —CO$_2$R$^2$ and Z is —P(O)(OR$^2$)(OR$^3$).

6. A compound of claim 1, wherein Y is —CO$_2$H and Z is —P(O)(OH)(OH).

7. A compound of claim 1, wherein R is alkenylene.

8. A compound of claim 1, wherein R is alkenylene of 8 to 15 carbon atoms.

9. A compound of claim 1, wherein X is —NR$^1$C(O)— or —C(O)NR$^1$— when p is 1; Y is —CO$_2$R$^2$; Z is —P(O)(OR$^2$)(OR$^3$); R is alkenylene, cinnamoyl or prenyl; R$^1$ is hydrogen or lower alkyl; R$^2$ and R$^3$ are each hydrogen; and n is 1 or 2.

10. A compound of claim 1, wherein X is —NHC(O)—, —NCH$_3$C(O)— or —C(O)NH— when p is 1; Y is —CO$_2$H; Z is —P(O)(OH)(OH); R is alkenylene; and n is 1 or 2.

11. A compound of claim 1, selected from the group consisting of:

(E,E)-6,10,14-Trimethyl-2-(phosphonomethyl)-5,9,13-pentadecatrienoic acid;

(E,E)-2-[(Dihydroxyphosphinyl)methyl]-3-oxo-3-[(3,7,11-trimethyl-2,6,10-dodecatrienyl)amino]-propanoic acid;

(E,E)-2-[(Dihydroxyphosphinyl)methyl]-5,9,13-trimethyl-4,8,12-tetradecatrienoic acid;

(E,E)-2-[(Dihydroxyphosphinyl)methyl]-7,11,15-trimethyl-6,10,14-hexadecatrienoic acid;

3-(Dodecylamino)-3-oxo-2-(phosphonomethyl)-propanoic acid;

(E)-3-[(3,7-Dimethyl-2,6-octenyl)amino]-3-oxo-2-(phosphonomethyl)-propanoic acid;

(E,E)-3-Oxo-2-(phosphonomethyl)-3-[(4,8,12-trimethyl-3,7,11-tridecatrienyl)-amino]-propanoic acid;

(E,E)-3-[Methyl-(3,7,11-trimethyl-2,6,10-dodecatrienyl)amino]3-oxo-2-(phosphonomethyl)-propanoic acid;

[S-(E,E)]-3-Phosphono-2-[(3,7,11-trimethyl-1-oxo-2,6,10-dodecatrienyl)amino]-propanoic acid;

[R-(E,E)]-3-Phosphono-2-[(3,7,11-trimethyl-1-oxo-2,6,10-dodecatrienyl)amino]-propanoic acid;

[S-(E,E)]-3-Phosphono-2-[(4,8,12-trimethyl-1-oxo-3,7,11-dodecatrienyl)amino])-propanoic acid;

[R-(E,E)]-3-Phosphono-2-[(4,8,12-trimethyl-1-oxo-3,7,11-dodecatrienyl]amino]-propanoic acid; and (E)-2-(Phosphonomethyl)-3-oxo-3-[(3,3,7,11-tetramethyl-6,10-dodecadienyl)amino]-propanoic acid.

12. A hypocholesterolemic or hypolipemic composition comprising a compound as defined in claim 1 and a pharmaceutically acceptable carrier therefor.

* * * * *